United States Patent
Lin et al.

(10) Patent No.: US 6,409,852 B1
(45) Date of Patent: Jun. 25, 2002

(54) BIOCOMPATIBLE LOW MODULUS TITANIUM ALLOY FOR MEDICAL IMPLANT

(75) Inventors: Jiin-Huey Chern Lin, Kaoshiung; Chien-Ping Ju, Room 607, No. 350, Tung Feng Rd., Tainan; Wen-Fu Ho, Tainan Hsien, all of (TW)

(73) Assignees: Jiin-Huey Chern, Kaohsiung; Chien-Ping Ju, Tainan, both of (TW)

( * ) Notice: Subject to any disclaimer, the term of this patent is extended or adjusted under 35 U.S.C. 154(b) by 0 days.

(21) Appl. No.: 09/226,204

(22) Filed: Jan. 7, 1999

(51) Int. Cl.[7] .................................................. C22F 1/18
(52) U.S. Cl. ............... 148/669; 148/421; 148/DIG. 76; 420/417; 420/421; 623/16.11; 623/23.53
(58) Field of Search ................................ 420/421, 417; 148/421; 623/16.11, 23.53

(56) References Cited

U.S. PATENT DOCUMENTS

| | | | | | |
|---|---|---|---|---|---|
| 4,857,269 | A | * | 8/1989 | Wang et al. ................. | 148/421 |
| 5,415,704 | A | * | 5/1995 | Davidson .................... | 148/238 |
| 5,906,692 | A | * | 5/1999 | Bhowal et al. ............. | 148/670 |
| 5,954,724 | A | * | 9/1999 | Davidson .................... | 148/421 |

* cited by examiner

*Primary Examiner*—Roy King
*Assistant Examiner*—Andrew Wessman
(74) *Attorney, Agent, or Firm*—Bacon & Thomas

(57) ABSTRACT

A biocompatible titanium alloy with low modulus comprising α" phase as a major phase and containing from about 6 to about 9 wt % of molybdenum, from 0 to about 1 wt % of an alloying element and the balance titanium. The alloying element is niobium and/or zirconium. The biocompatible titanium alloy is suitable for use as a material for a medical prosthetic implant.

11 Claims, 20 Drawing Sheets

BIOCOMPATIBLE LOW MODULUS TITANIUM ALLOY FOR MEDICAL IMPLANT

FIELD OF THE INVENTION

The present invention relates to low modulus biocompatible titanium alloys suitable for use as a material for a medical prosthetic implant, and in particular to a biocompatible titanium alloy comprising α" phase as a major phase and the process of preparing the same.

DESCRIPTION OF THE RELATED ART

Concern has been raised from time to time about the stress shielding phenomenon, i.e., insufficient loading of bone due to the large difference in modulus between implant device and its surrounding bone. This phenomenon, more often observed in cementless hip and knee prostheses (Sumner et al., 1992), can potentially lead to bone resorption (Engh et al., 1988) and eventual failure of the arthroplasty (Sumner et al., 1992).

Both strain gauge analysis (Lewis et al., 1984) and finite element analysis (Koeneman et al., 1991) have demonstrated that lower modulus (more flexible) hips produce stresses and strains that are closer to those of the intact femur, and a lower modulus hip prosthesis may better simulate the natural femur in distributing stress to the adjacent bone tissue (Cheal et al., 1992; Prendergast et al, 1990). Canine and sheep implantation studies have shown significantly reduced bone resorption in animals with low modulus hips (Bobyn et al., 1992), and the bone remodeling commonly experienced by hip prosthesis patients may be reduced by a prosthesis having lower modulus (Bobyn et al., 1990 and 1992).

Titanium and titanium alloys have become one of the most attractive implant materials due to their light weight, high biocorrosion resistance, biocompatibility and mechanical properties, including low modulus. For example, the most widely used titanium alloy, Ti-6Al-4V, according to Pilliar (Pilliar, 1990), has an elastic modulus (108 GPa) only about half that of 316L stainless steel (200 GPa) or Co—Cr—Mo alloy (210 GPa) that is still popularly used today.

Although alpha-beta type Ti-6Al-4V alloy is widely used as an implant material, studies have reported that the release of Al and V ions from the alloy might cause some long term health problems (Rao, 1996, Yumoto, 1992, Walker 1989, McLachlan et al., 1983). Moreover, the low wear resistance of Ti-6Al-4V could accelerate the release of such harmful ions (Wang et al., 1996, McKellop, 1990, Rieu, 1992).

Recently much research effort was devoted to the study of more biocompatible, lower modulus, better processability beta or near-beta Ti alloys, such as Ti-13Nb-13Zr (Mishra 1996), Ti-11.5Mo-6Zr-2Fe (Wang 1996) and Ti-15Mo (Zardiackas et al. 1996). The near-β Ti-13Nb-13Zr alloy issued to Davidson et al (U.S. Pat. No. 5169597, 1992), was reported to consist of hexagonal martensite phase under water-quenched condition. With subsequent aging, the bcc β phase was precipitated. This aged Ti-13Nb-13Zr alloy had a lower (by 30–40%) modulus than mill-annealed Ti-6Al-4V alloy (Mishra et al., 1996).

The β phase Ti-15Mo alloy is being evaluated for orthopaedic implant applications by Synthes USA. The rapidly quenched Ti-15Mo alloy was reported to have a fine-grained bcc structure with a lower modulus (77.7 GPa) than those of 316L stainless steel, Grade IV Ti, Ti-6Al-4V and Ti-6Al-7Nb (Zardiackas et al., 1996).

SUMMARY OF THE INVENTION

It is therefore an object of the invention to provide a biocompatible titanium alloy having even lower modulus, equivalent strength and appropriate hardness, suitable for use in a wide range of medical implant applications.

It has been found by the inventors that titanium alloy comprising from about 5 to about 10 wt % of molybdenum if subject to fast cooling can induce a significant amount of α" phase. The titanium alloy having a martensite structure α" phase exhibits a desirable combination of properties, i.e. low modulus of elasticity, equivalent bending strength and appropriate hardness.

It has also been found by the inventors that addition of alloying elements, i.e. niobium and zirconium into the Ti—Mo system can increase the bending strength while maintaining the low modulus of elasticity.

Specifically, the biocompatible titanium alloy of the invention includes from about 5 to about 10 percent by weight of molybdenum, from 0–3 percent by weight of an alloying element and the balance titanium. The alloying element is niobium (Nb) or zirconium (Zr) or the mixture of the two elements.

In case small size or complicated prosthetic implants are fabricated, the alloy is first melted at a temperature greater than 1750° C. The molten titanium alloy is then directly cast into a mold of desired shape in a vacuum or inert atmosphere, with a cooling rate greater than 10° C./second.

In case simple shape prosthetic implants are fabricated, the alloy is first subjected to cold or hot working, including rolling, drawing, extrusion or forging, followed by annealing at a temperature of 600–1200° C. and fast cooling at a cooling rate greater than 10° C./second to obtain the α" phase.

According to an aspect of the invention, the titanium alloy preferably comprises 6–9 wt % of molybdenum. The Ti-7.5 wt % Mo alloy exhibits very low modulus of elasticity, very high springback capability, equivalent bending strength and appropriate micorhardness. Specifically, the Ti-7.5 wt % Mo alloy shows a bending modulus of 55 GPa which is closer to the modulus of human long bone, 20 GPa.

According to another aspect of the invention, when 1 wt % of Nb or Zr is added, the acicular martensitic structure of α" phase of the titanium alloy remains, microhardness increases 25–29%, bending strength increases 13–21% while the modulus and springback capability only slightly change.

BRIEF DESCRIPTION OF THE DRAWINGS

The invention is hereinafter described in detail by reference to the non-limiting examples and the accompanying drawings in which.

DETAILED DESCRIPTION OF THE INVENTION

EXAMPLE 1–7

A series of titanium alloys containing 3, 5, 6, 7.5, 9, 10, and 15 wt % of molybdenum were prepared from titanium of 99.9% in purity and molybdenum of 99.95% using a commercial arc-melting vaccum-pressure type casting system (Castmatic, Iwatani Corp., Japan). The melting chamber was first evacuated and purged with argon. An argon pressure of 1.5 kgf/cm$^2$ was maintained during melting. Appropriate amounts of metals were melted in a U-shaped copper hearth with a tungsten electrode. The ingots were re-melted three times prior to casting to improve chemical homogeneity.

Prior to casting, the ingots were re-melted again in an open-based copper hearth under an argon pressure of 1.5 kgf/cm$^2$. The difference in pressure between the two chambers allowed the molten alloys to instantly drop into a graphite mold when melted.

The cast alloys were sectioned using a Buehler Isomet low speed diamond saw to obtain specimens for various purposes. Surfaces of the alloys for microstructural study were mechanically polished via a standard metallographic procedure to a final level of 0.3 µm alumina powder, then etched in a solution of water, nitric acid, and hydrofluoric acid (80:15:5 in volume). Microstructure of the etched alloys was examined using an optical microscope (MC80, ZEISS, Germany). The results are shown in FIGS. 1b–1h.

Figure 2:
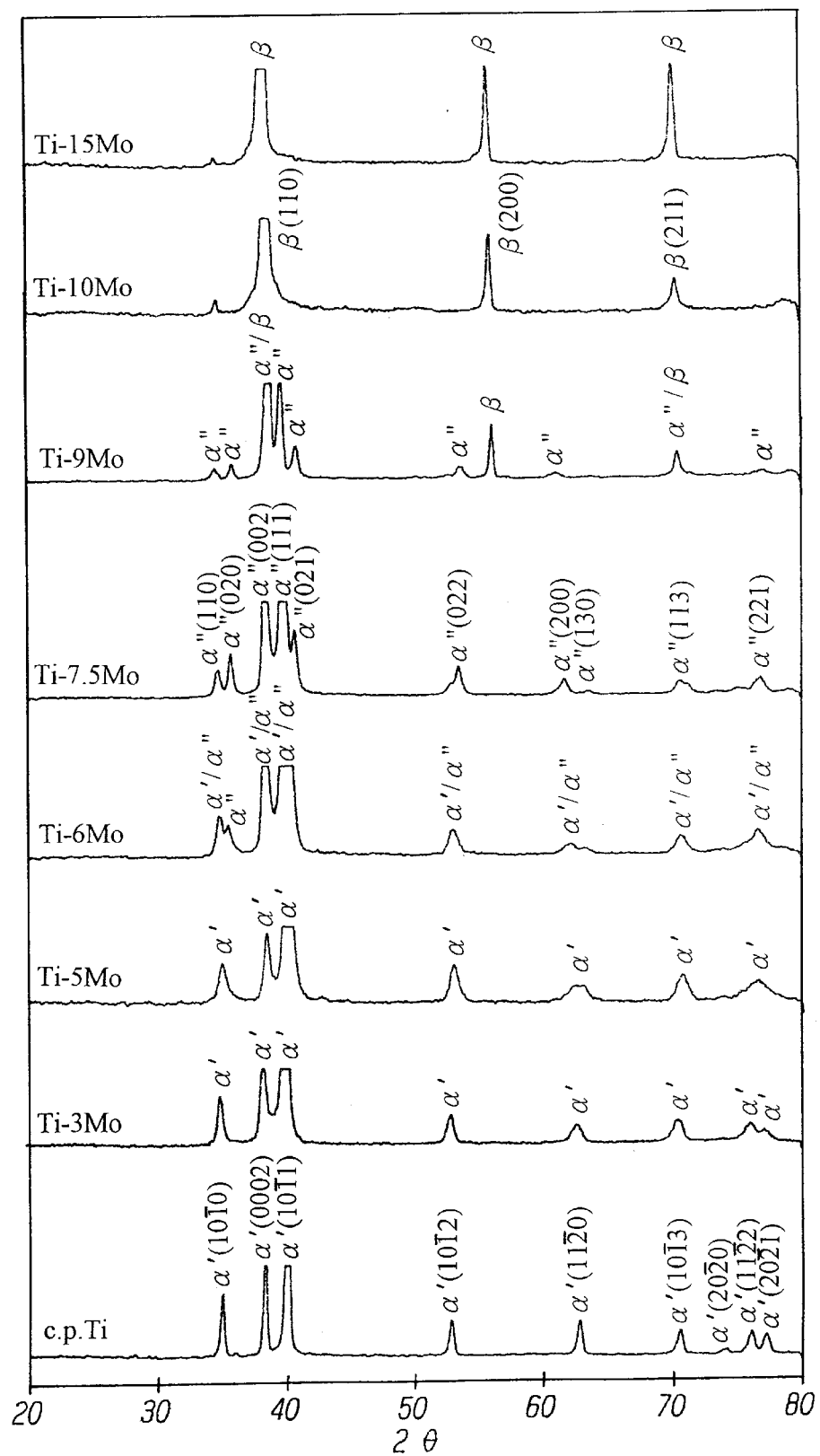
FIG. 2 is a diagram showing X-ray diffraction patterns of c.p. Ti and Ti—Mo alloys.
Figure 3:
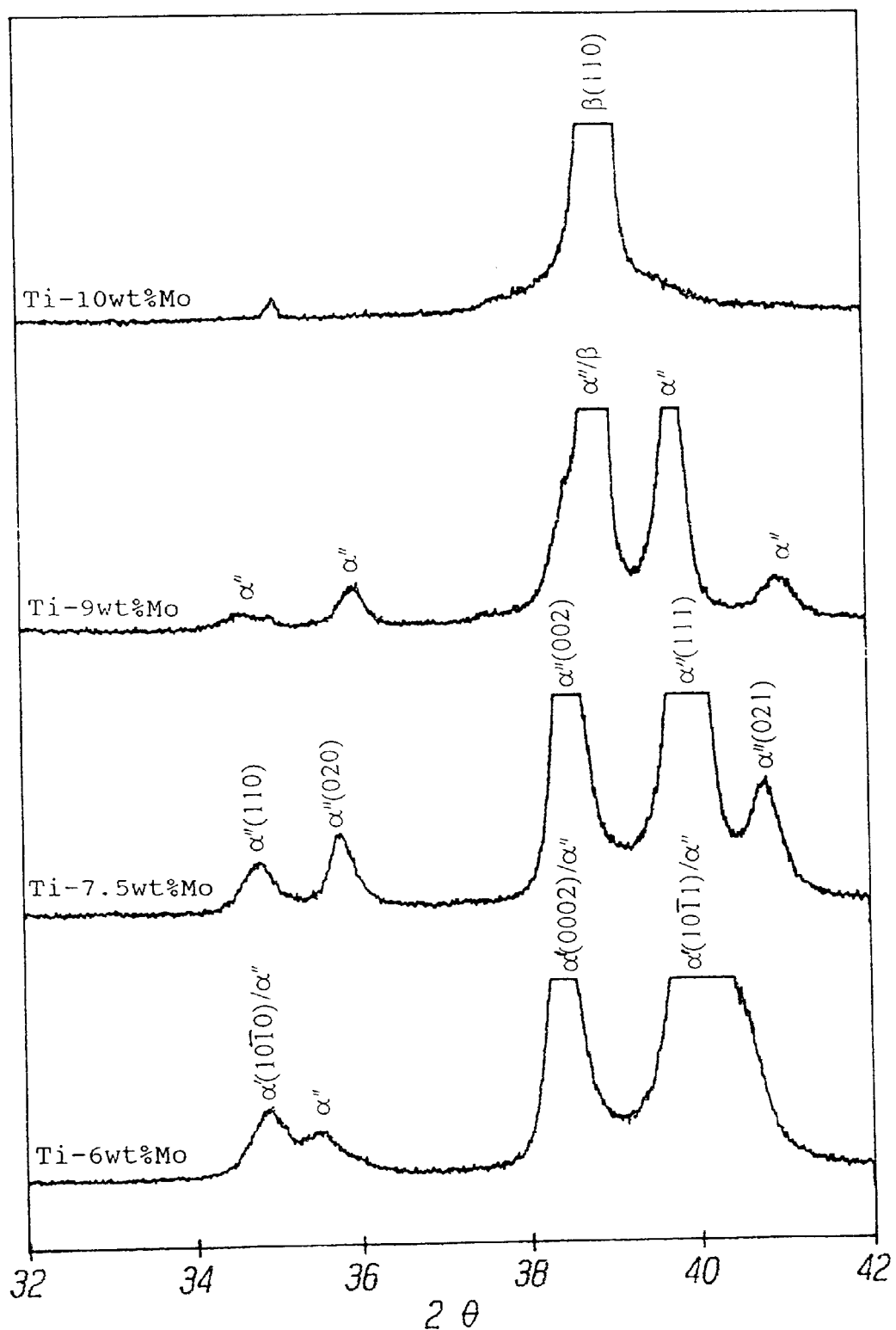
FIG. 3 is a diagram showing X-ray diffraction patterns of Ti—Mo alloys at low scanning speed.

X-ray diffraction (XRD) for phase analysis was conducted using a Rigaku diffractometer (Rigaku D-max IIIV, Rigaku Co., Tokyo, Japan) operated at 30 kV and 20 mA. A Ni-filtered CuKα radiation was used for this study. Phases were identified by matching each characteristic peak with the JCPDS files. The results are shown in FIGS. 2 and 3 and summarized in Table 1 below.

TABLE 1

| wt % Mo | phase | crystal structure |
| --- | --- | --- |
| c.p.Ti | α' | hexagonal |
| 3–5 | α' | hexagonal |
| 6 | α'/α" | hexagonal/orthorhombic |
| 7.5 | α" | orthorhombic |
| 9 | α"/β | orthorhombic/bcc |
| 10–20 | β | bcc |

Figure 4:
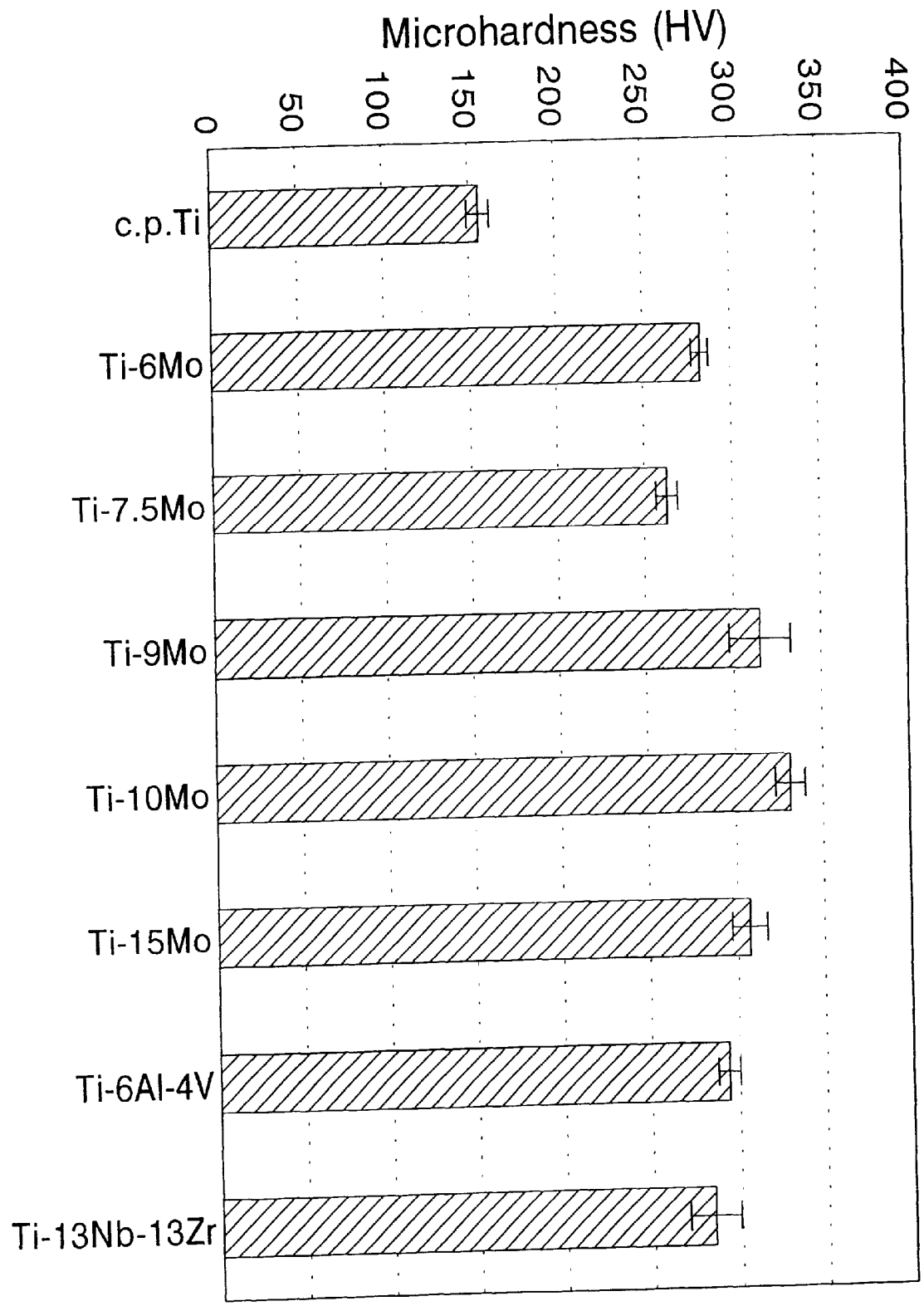
FIG. 4 is a diagram showing microhardness of c.p. Ti and Ti—Mo alloys.

The microhardness of polished alloys was measured using a Matsuzawa MXT70 microhardness tester with a load of 200 gm for 15 seconds. The results are shown in FIG. 4.

Figure 5:
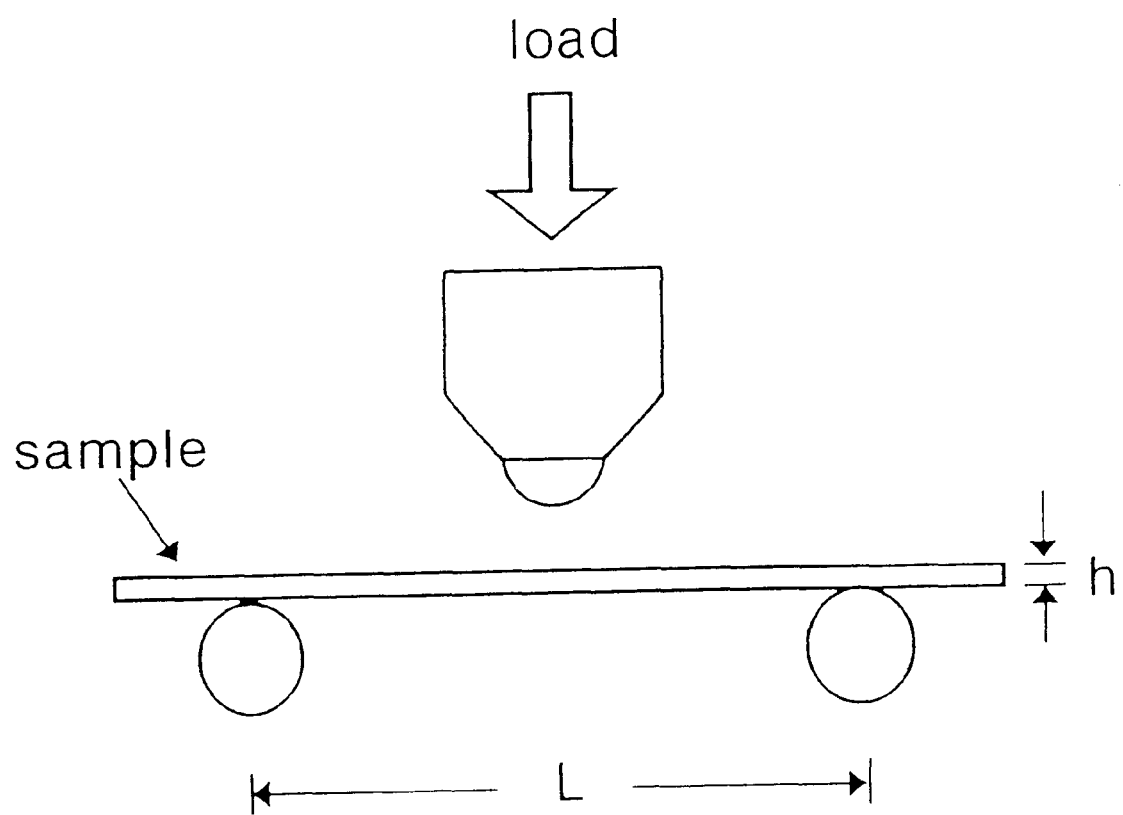
FIG. 5 is a schematic diagram showing the bending test used in Examples 1–4.

Three-point bending tests were performed using a desktop mechanical tester (Shimadzu AGS-500D, Tokyo, Japan). A schematic diagram of the bending test is shown in FIG. 5. The bending strengths were determined using the equation [Metals Handbook 9th ed.]:

$$\sigma = \frac{3PL}{2bh^2}$$

where σ is bending strength (MPa); P is load (Kg); L is span length (mm); b is specimen width (mm); and h is specimen width (mm). The modulus of elasticity in bending is calculated from the load increment and the corresponding deflection increment between the two points on the straight line as far apart as possible using the equation:

$$E = \frac{L^3 \Delta P}{4bh^3 \Delta \delta},$$

where E is modulus of elasticity in bending (Pa); ΔP is load increment as measured from preload (N); and Δδ is deflection increment at midspan as measured from preload. The average bending strength and modulus of elasticity in bending were taken from at least five tests under each condition. The results are respectively shown in FIG. 6 and FIG. 7.

Figure 8:
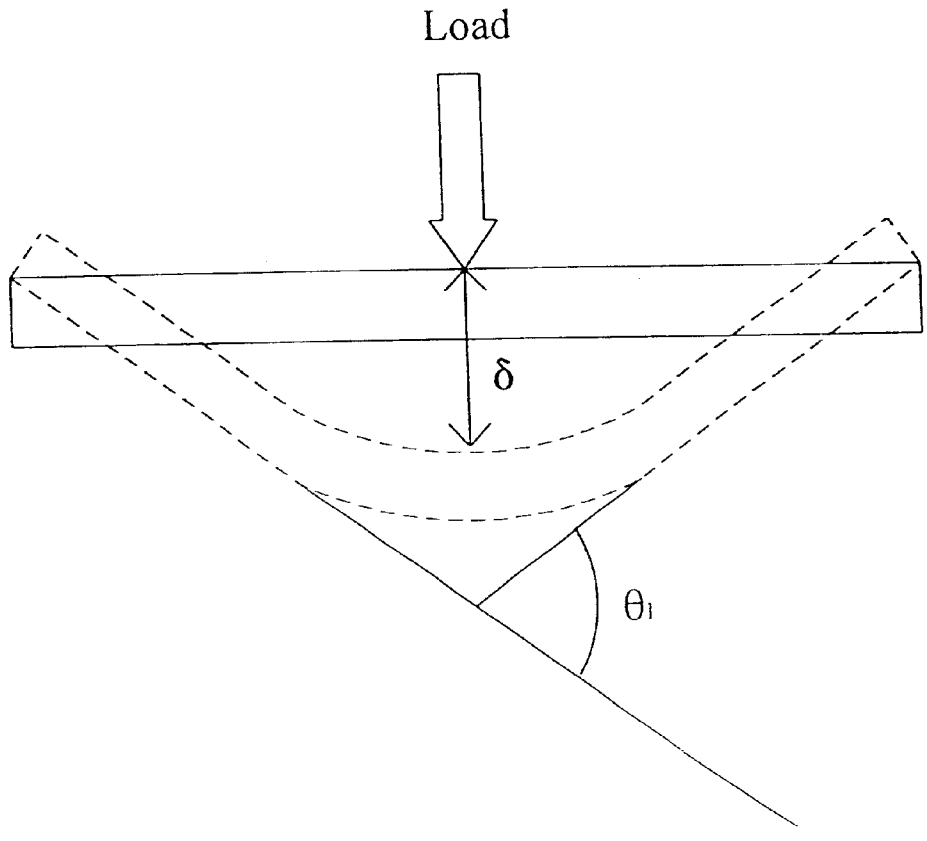
FIG. 8 is a schematic diagram illustrating elastic recovery measurement.
Figure 8:
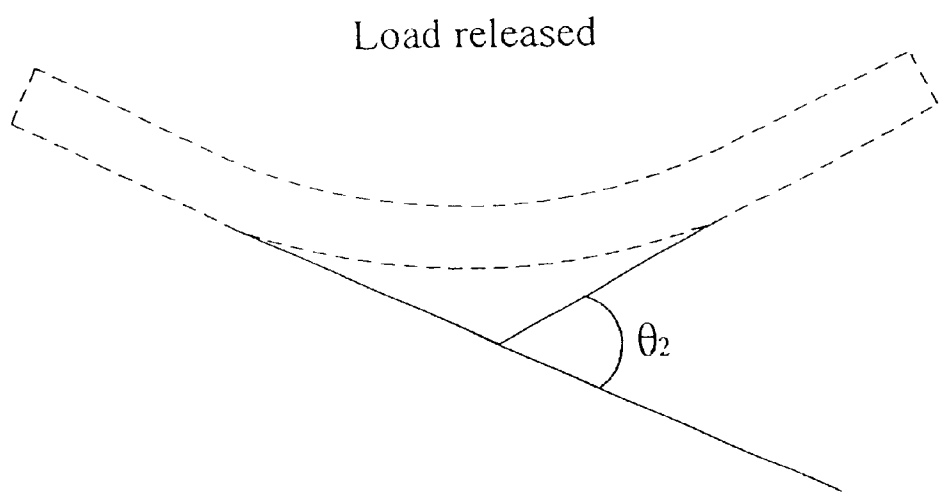
Figure 9:
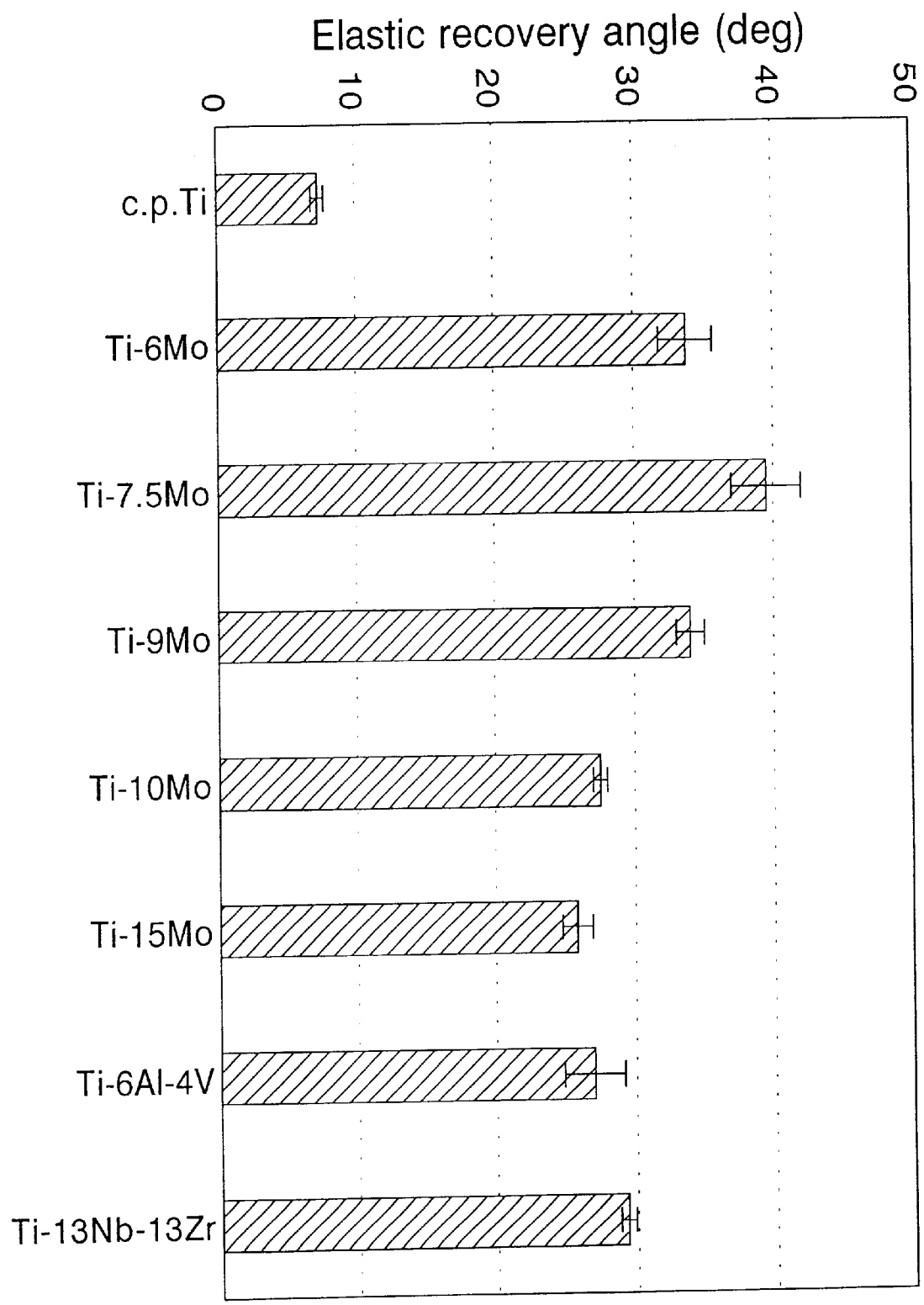
FIG. 9 is a diagram showing elastic recovery angles of c.p. Ti and Ti—Mo alloys.

The elastic recovery (springback) capability for each material was evaluated from the change in deflection angle when loading was removed. As schematically shown in FIG. 8, the springback capability is a measurement of $\theta_1 - \theta_2$, wherein $\theta_1$ is the deflection angle somewhere in the plastic deflection regime and $\theta_2$ is the angle after loading is released. The results are shown in FIG. 9.

COMPARATIVE EXAMPLE 1

Figures 1A, 1B:
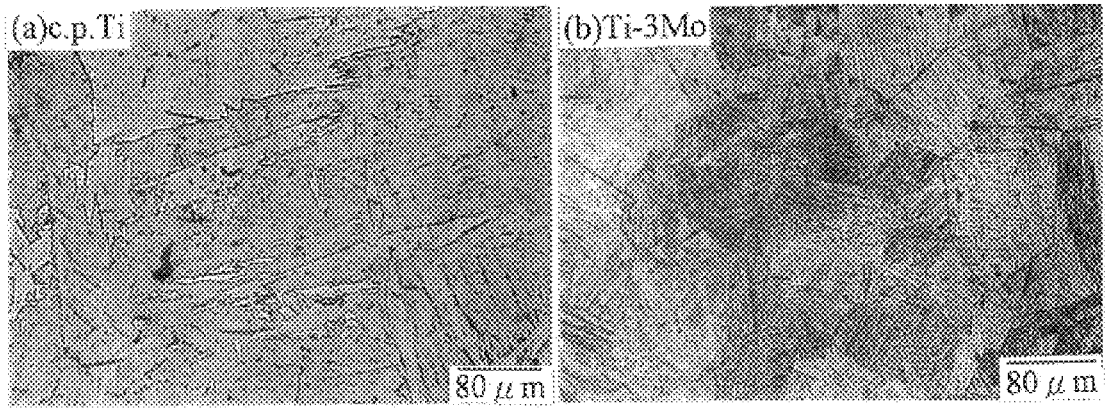
FIG. 1a is a light micrograph of c.p. Ti.
FIGS. 1b–1h are respectively micrographs of Ti-3 wt % Mo, Ti-5 wt %, Ti-6 wt % Mo, Ti-7.5 wt % Mo, Ti-9 wt % Mo, Ti-10 wt % Mo and Ti-15 wt % Mo.
Figures 1C, 1D:
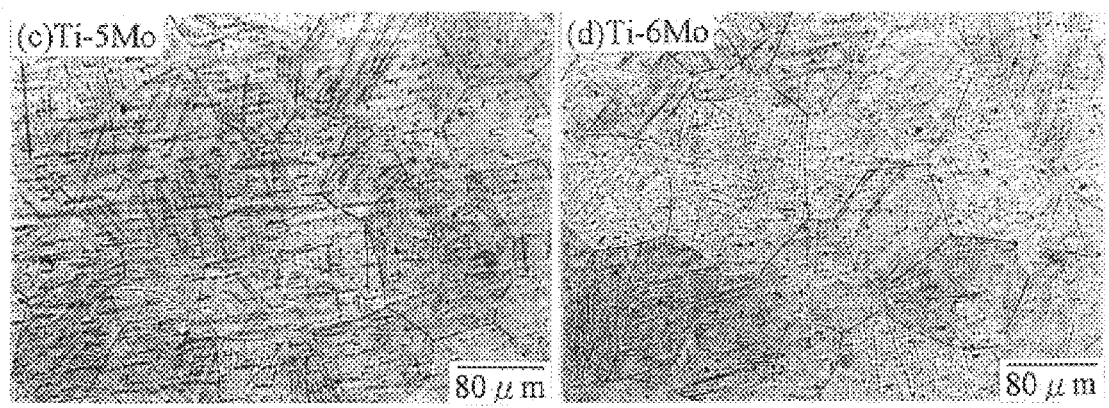
Figure 1E:
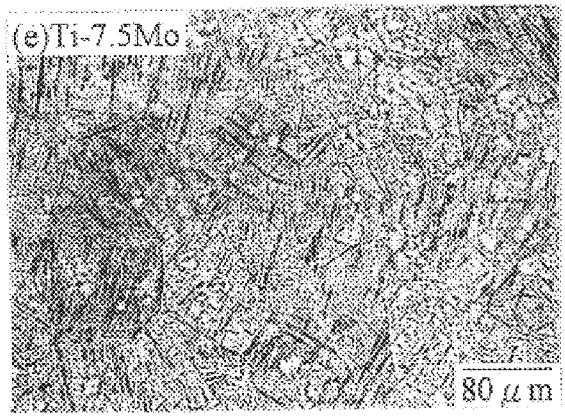
Figure 1F:
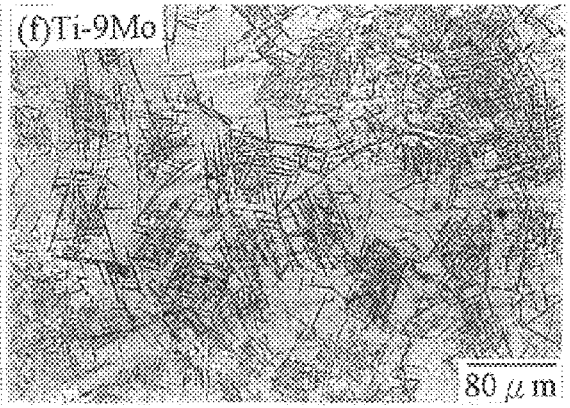
Figure 1G:
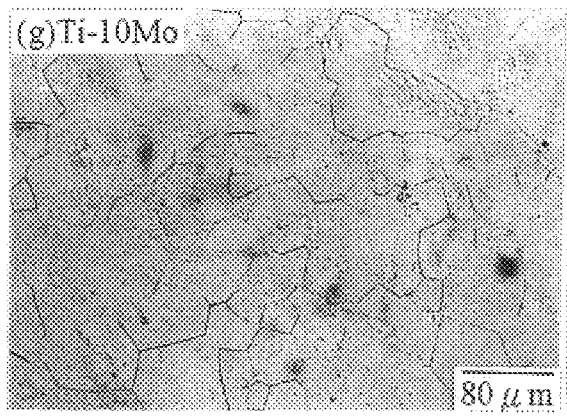
Figure 1H:
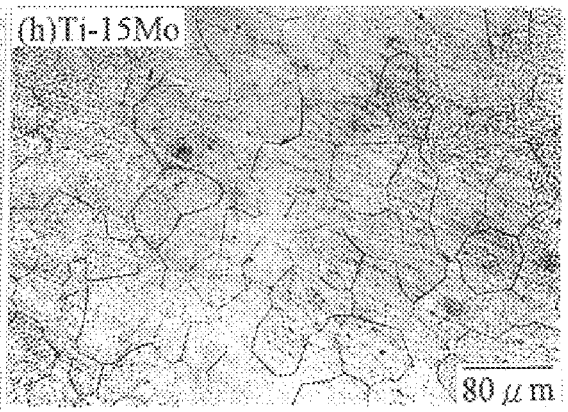

In this comparative example, titanium of 99.9% in purity (c.p.Ti) was sectioned by the same procedures as set forth in Examples 1–7 to obtain specimens. Microstructure of the specimens was examined by using the same optical microscope and the result is shown in FIG. 1a. The X-ray diffraction pattern, the microhardness, the bending strength and bending modulus were also tested by the same procedures as set forth in Examples 1–7 and the results are respectively shown in FIG. 2 , FIG. 4, FIG. 6, and FIG. 7.

As can be seen from FIG. 2 and Table 1, crystal structure of the binary Ti—Mo alloy is sensitive to the composition (molybdenum content) of the alloy. The c.p. Ti was comprised entirely of a hexagonal α' phase. When 6 wt % Mo was contained, the orthorhombic α" phase was observed in the cast alloy, as indicated in the splitting of the single α' (1 0–1 0) peak into two α" peaks. When 7.5 wt % Mo was contained, the cast alloy was entirely made up of α" phase. When the Mo content increased to 9 wt %, a significant amount of β phase was retained. When the Mo content increased to 10 wt % or higher, only the retained β phase was observed in the XRD patterns.

The sensitive dependence of phase/crystal structure on alloy composition in the range between 6 and 10 wt % Mo can be seen more clearly in a low scanning speed (0.5°/min) XRD patterns (FIG. 3). The splitting of XRD peaks is a direct indication of the existence of orthorhombic α" phase that distorted the unit cell and decreased its symmetry level. FIG. 3 also showed that α" peaks shifted towards high angle direction with increasing Mo content. This indicates a decrease in planar spacings of the α" phase.

The microstructure of c.p. Ti and the series of Ti—Mo alloys, as shown in FIGS. 1a–1h, was consistent with the XRD results. The hexagonal c.p. Ti exhibited a typical rapidly-cooled metastable feather-like microstructure. When 6 wt % Mo was contained, the fine, acicular martensitic structure of α" phase was observed. When 7.5 wt % Mo was contained, the entire alloy was dominated by the martensitic α" structure. When the Mo content increased to 9 wt %, a significant amount of equi-axed, retained β phase was observed. When the alloy contained 10 wt % or more Mo, β phase became the only dominant phase.

As shown in FIG. 4, all the Ti—Mo alloys (containing 6–15 wt % Mo) had much higher microhardness values (270–330 HV) than that of c.p. Ti (160 HV). Among all Ti—Mo alloys, the α" phase alloy (Ti-7.5 Mo) had the lowest microhardness value (263 HV), while the β phase alloy (especially the alloy containing 10 wt % Mo) had the highest hardness. The microhardness value of Ti-7.5Mo was also lower than those of Ti-6Al-4V (294HV) and Ti-13Nb-13Zr (285 HV) by 10.5 and 7.7%, respectively. The low microhardness of Ti-7.5Mo demonstrates an advantage in reducing the wear of its soft counterpart (e.g., polyethylene socket), when used as an implant material, such as an artificial hip joint.

Figure 6:
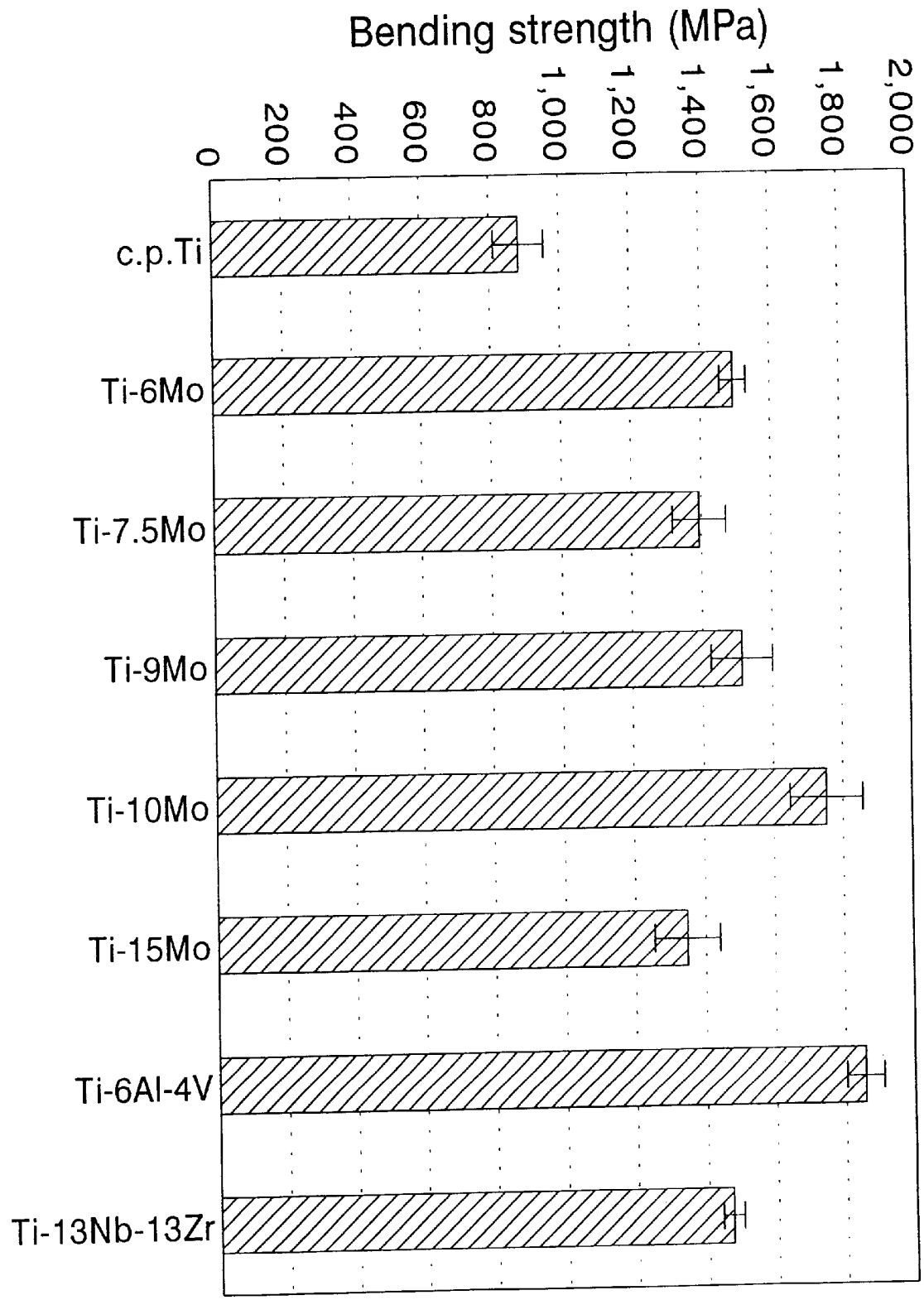
FIG. 6 is a diagram showing bending strength of c.p. Ti and Ti—Mo alloys.

Like microhardness, the bending strengths of all the Ti—Mo alloys (1400–1750 MPa) were much higher than that of c.p. Ti (880 MPa), as shown in FIG. 6. Though lower than that of Ti-6Al-4V, the bending strength of Ti-7.5Mo was similar to those of Ti-13Nb-13Zr, and higher than c.p. Ti by nearly 60%.

The dependence of modulus was more sensitive on phase/crystal structure than on other factors. The results of the present invention strongly suggest that the orthorhombic α" phase (with Mo contents close to 7.5 wt %) has a lower modulus than all other phases in the binary Ti—Mo system.

Figure 7:
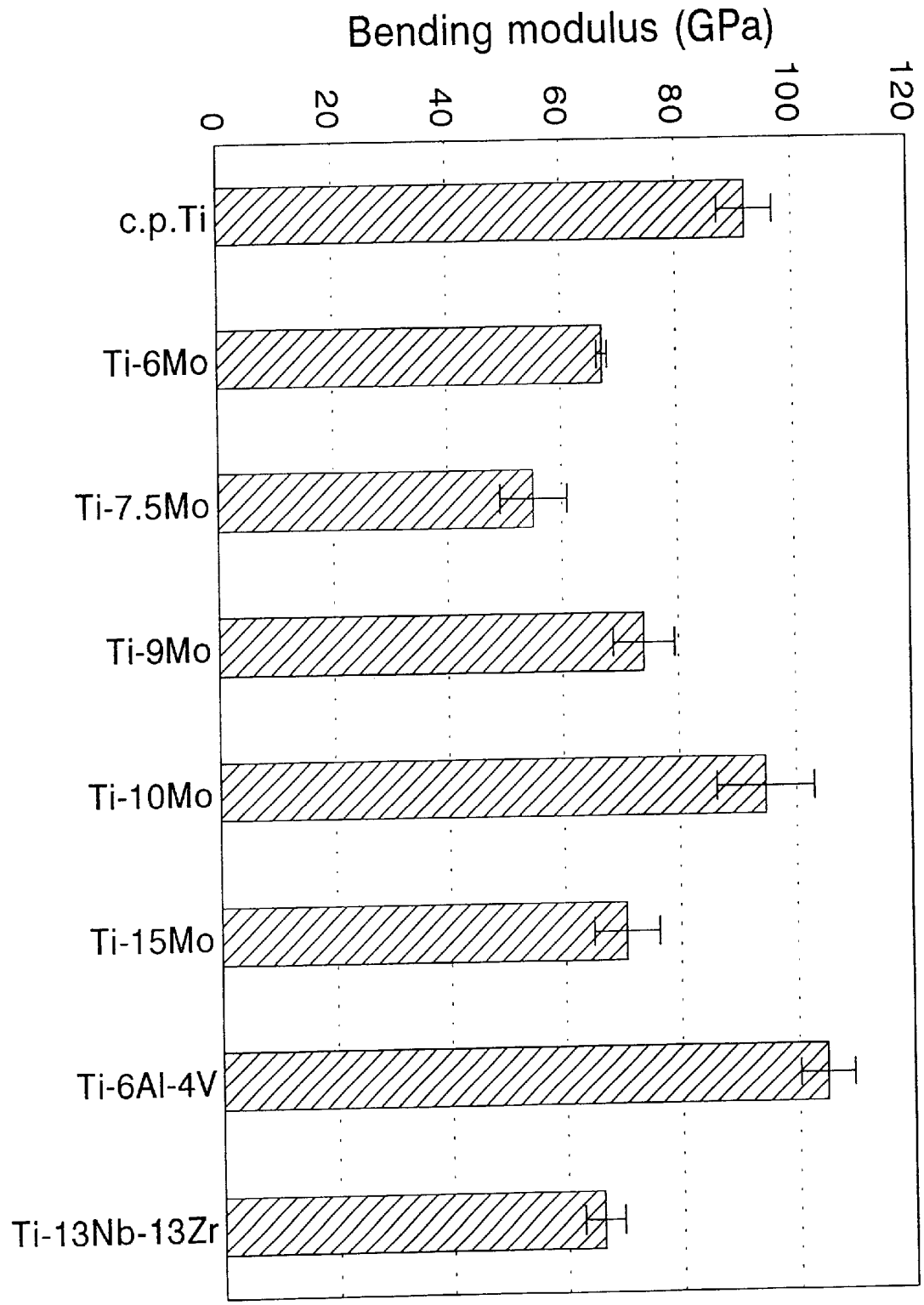
FIG. 7 is a diagram showing bending moduli of c.p. Ti and Ti—Mo alloys.

It is well known that β phase Ti alloys generally have a lower modulus level than α or α/β type alloys (Zardiackas et al., 1996). It is worth noting that the bending modulus of the α"-dominated Ti-7.5Mo alloy (55 GPa) was even lower than all β phase Ti—Mo alloys as shown in FIG. 7. This bending modulus was lower than Ti-15Mo by 22%, than Ti-6Al-4V by 47%, than c.p. Ti by 40%, and than Ti-13Nb-13Zr by 17%. As mentioned earlier, using an implant material with low modulus, such as Ti-7.5 Mo, can reduce the stress shielding effect.

The advantage in mechanical properties of Ti-7.5 Mo alloy is also demonstrated in its high elastic recovery capability. High elastic recovery (springback) capability of a material is an indication of high strength and low modulus and is essential for many loading-bearing implant and dental applications. As shown in FIG. 9, the elastic recovery capability of Ti-7.5 Mo was greater than all other Ti alloys fabricated in these examples. For example, the elastically recoverable angle of Ti-7.5 Mo was higher than Ti-15Mo by 53%, than Ti-6Al-4V by 46%, than Ti-13Nb-13Zr by 35%, and than c.p. Ti by as much as 440%.

The microhardness and bending properties of c.p. Ti and a variety of Ti alloys used or potentially used as implant material are summarized in Table 2 below. Such advantages as low hardness, low modulus and high elastic recovery capability of the α" phase Ti-7.5 Mo alloy are clearly demonstrated in the table. In the current search of a better implant material, the low hardness, low modulus, excellent elastic recovery capability and reasonably high strength α"-dominated Ti-7.5 Mo alloy serves as a new promising candidate.

TABLE 2

|  | Microhardness (HV) | Bending strength (Mpa) | Bending modulus (Gpa) | Elastic recovery angle (deg) |
| --- | --- | --- | --- | --- |
| c.p. Ti | 156 | 884 | 92 | 7 |
| Ti-6Al-4V | 294 | 1857 | 105 | 27 |
| Ti-13Nb-13Zr | 285 | 1471 | 66 | 29 |
| Ti-15Mo | 307 | 1348 | 71 | 26 |
| Ti-7.5Mo | 263 | 1395 | 55 | 40 |

EXAMPLE 8–9

In these examples, 1 wt % of alloying elements: Zr (α-stabilizer), Nb (β stabilizer) each of 99.95% in purity were added into Ti-7.5 Mo. Ti-7.5Mo-1Nb and Ti-7.5Mo-1Zr alloys were prepared from 99.9% pure titanium and 99.95% pure molybdenum using a commercial arc-melting vacuum-pressure type casting system (Castmatic, Iwatani Corp., Japan). The melting chamber was first evacuated and purged with argon. An argon pressure of 1.5 kgf/cm$^2$ was maintained during melting. Appropriate amounts of metals were melted in a U-shaped copper hearth with a tungsten electrode. The ingots were re-melted three times to improve chemical homogeneity.

Prior to casting, the ingots were re-melted again in an open-based copper hearth under an argon pressure of 1.5 kgf/cm$^2$. The difference in pressure between the two chambers allowed the molten alloy to quickly drop into a room temperature graphite mold as soon as the alloy was melted.

Figure 10A:
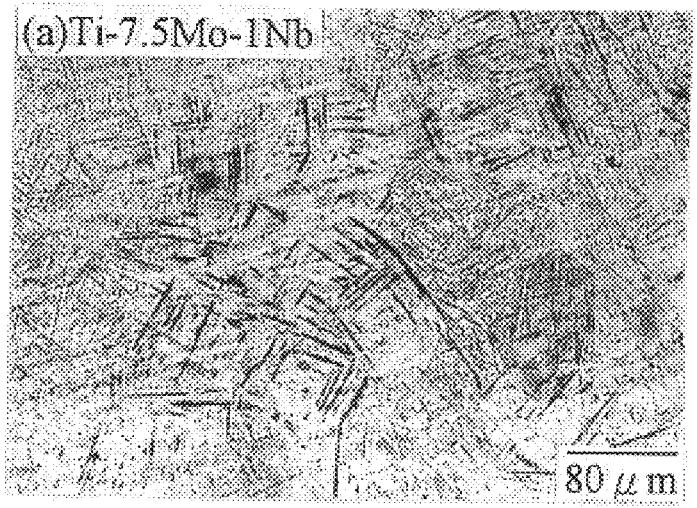
FIGS. 10a–10b are respectively micrographs of Ti-7.5Mo-1Nb and Ti-7.5Mo-1Zr alloys.
Figure 10B:
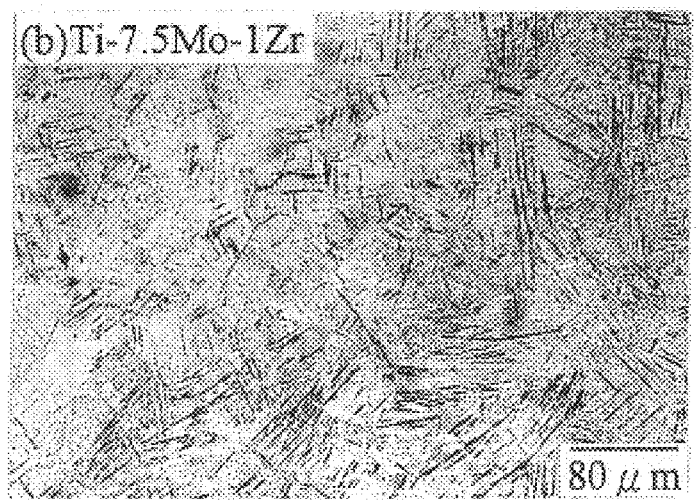

Surfaces of the cast alloys for microstructural study were mechanically polished via a standard metallographic procedure to a final level of 0.3 μm alumina powder, then etched in a solution of water, nitric acid, and hydrofluoric acid (80:15:5 in volume). Microstructure of the etched alloys was examined using an optical microscope (MC80, ZEISS, Germany). The results are illustrated in FIG. 10a and FIG. 10b.

X-ray diffraction (XRD) for phase analysis was conducted using a Rigaku diffractometer (Rigaku D-max IIIV, Rigaku Co., Tokyo, Japan) operated at 30 kV and 20 mA. A Ni-filtered CuK$_α$ radiation was used for this study. Phases were identified by matching each characteristic peak with the JCPDS files. The results are shown in FIG. 9.

Figure 11:
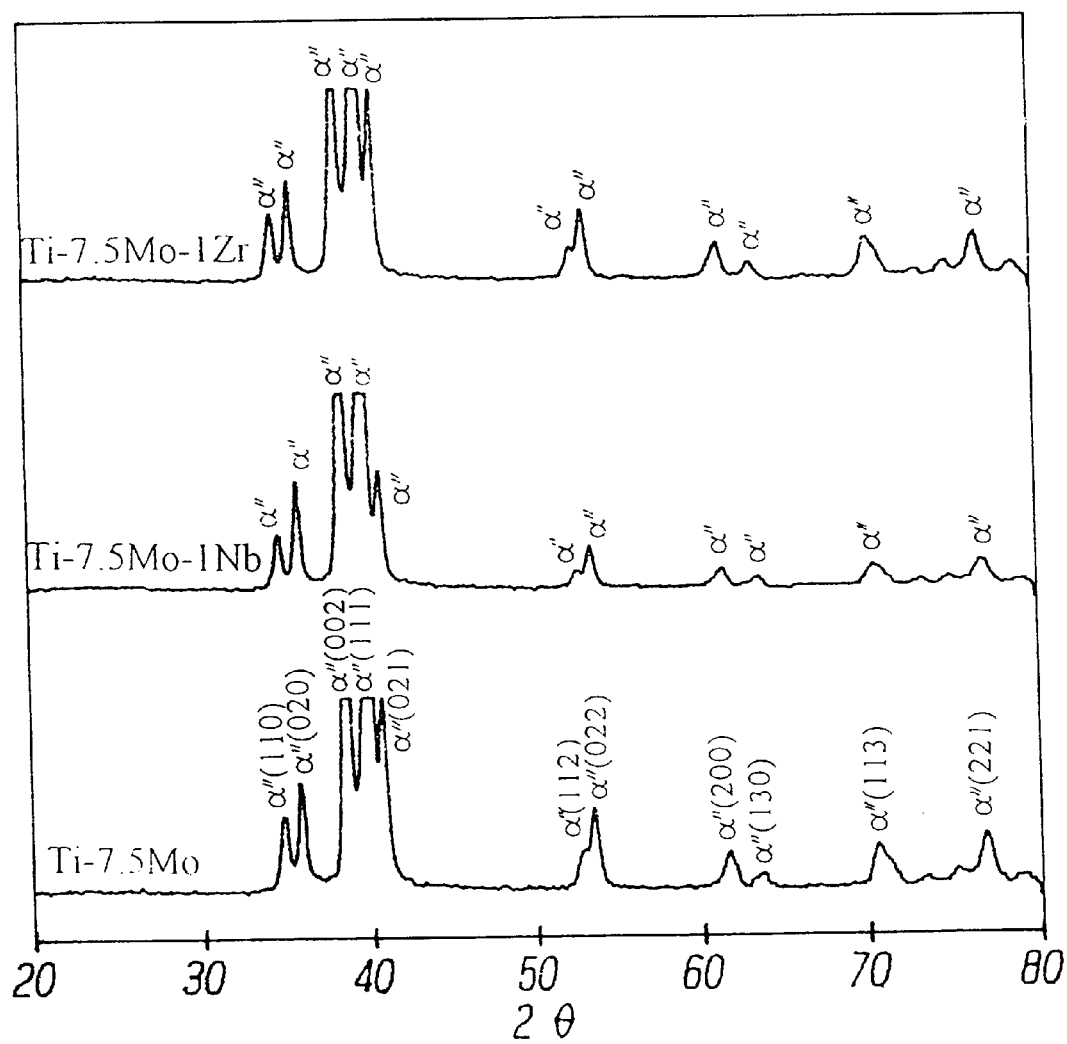
FIG. 11 is a diagram showing XRD patterns of Ti-7.5Mo-1Nb and Ti-7.5Mo-1X alloys.
Figure 12:
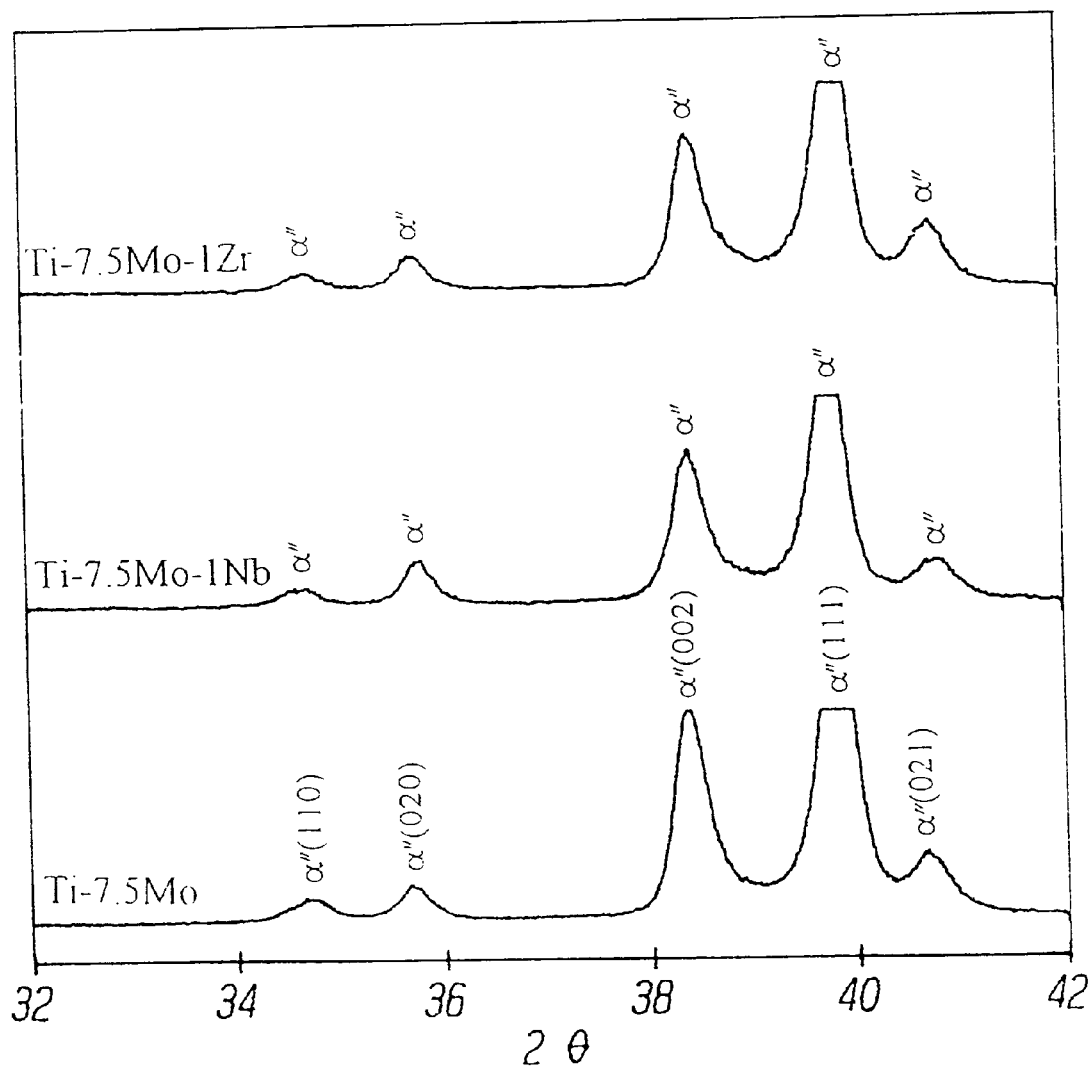
FIG. 12 is a diagram showing XRD patterns of Ti-7.5Mo and Ti-7.5Mo-1X alloys at lower scanning speed.

The microhardness of polished alloys was measured using a Matsuzawa MXT70 microhardness tester at 200 gm for 15 seconds. The results are shown in FIG. 11 and FIG. 12.

Three-point bending tests were performed by using a desk-top mechanical tester (Shimadzu AGS-500D, Tokyo, Japan). A schematic diagram showing the bending test has been shown in FIG. 5. The bending strengths were determined using the equation $\alpha = 3PL/2bh^2$. The modulus of elasticity in bending was calculated from the load increment and the corresponding deflection increment between two points on a straight line as far apart as possible using the equation $E = L^3 \Delta P / 4bh^3 \Delta \delta$. Average bending strength and modulus were obtained from at least five tests for each condition. The elastic recovery (springback) capability for each material was evaluated from the change in deflection angle when loading was removed. As schematically shown in FIG. 8, the springback capability is a measurement of $\theta_1 - \theta_2$, where $\theta_1$ is the deflection angle somewhere in the plastic deformation regime and $\theta_2$ is the angle after loading is released. The results of the measured bending strength, bending modulus and elastic recovery angles are summarized in Table 3 below.

TABLE 3

| | Microhardness | Bending strength | Bending modulus | Elastic recovery angle (deg) |
|---|---|---|---|---|
| Ti-7.5Mo-1Nb | 311 | 1663 | 65 | 37 |
| Ti-7.5Mo-1Zr | 320 | 1546 | 67 | 33 |

COMPARATIVE EXAMPLE 2

In this comparative example, titanium of 99.9 % in purity (c.p.Ti) was sectioned by the same procedures as set forth in Examples 8–9 to obtain specimens. Microstructure of the specimens was examined by using the same optical microscope and the results were shown in FIG. 10. The X-ray diffraction pattern, the microhardness, the bending strength, bending modulus and elastic recovery angles were also tested by the same procedures as set forth in Examples 7–8 and the results are respectively shown in FIG. 11.

As shown in FIGS. 11 and 12, Ti-7.5Mo was a typical orthorhombic α" phase alloy, as mentioned earlier. Again, the splitting of XRD peaks was a direct indication of the existence of orthorhombic α phase.

As 1 wt % Zr or Nb was introduced into the alloy, the XRD patterns essentially remained unchanged. This indicated that the inherently low modulus α" phase was still dominant in Ti-7.5Mo-1Zr and Ti-7.5Mo-1Nb alloys. Even being a β stabilizer, the small amount of Nb did not cause noticeable phase change.

The microstructure of Ti-7.5Mo-1Nb and Ti-7.5Mo-Zr alloys, as shown in FIG. 10, was consistent with the XRD results. The microstructure of Ti-7.5Mo-1Nb (FIG. 10a) and Ti-7.5Mo-1Zr (FIG. 10b) alloys was very similar to that of Ti-7.5Mo.

As shown in Table 3, when 1 wt % Nb or Zr was added to Ti-7.5 Mo, the microhardness increased to 310–320 HV, that was close to that of Ti-6Al-4V and a little higher than those of Ti-15Mo and Ti-13Nb-13Zr. These and XRD results indicate that the retained β phase has a higher hardness level than α" phase. The more β phase was present, the harder the alloy became.

As shown in Table 3, when 1 wt % Nb or Zr was added, the bending strength increased to 1663 and 1546 MPa, respectively. These results suggest that the retained β phase has a higher strength level than α" phase. The more β phase was present, the stronger the alloy became.

As shown in Table 3, when 1 wt % Nb or Zr was added, the bending modulus slightly increased to 65–67 GPa, that was close to that of Ti-13Nb-13Zr. These and XRD results suggest that the retained β phase has a higher modulus level than α phase. The more β phase was present, the stiffer the alloy became.

It is interesting to note that cast Ti-7.5Mo-1Nb and Ti-7.5Mo-1Zr alloys exhibited higher strengths than Ti-7.5Mo, Ti-15Mo and Ti-13Nb-13Zr, while maintaining their low moduli. Again, this is due to the maintaining of an α" phase in these two alloy systems.

As shown in Table 3, the elastically recoverable angle of Ti-7.5Mo-1Nb and Ti-7.5Mo-1Zr were also similar to that of Ti-7.5Mo alloy.

It can be seen from the above examples and description, when 1 wt % Zr or Nb was added, the fine, acicular martensitic structure of α phase remained, microhardness increased 25–29%, bending strength increased 13–21%, while modulus and elastic recovery angles only slightly changed.

EXAMPLE 10

A titanium alloy containing 7.5 wt % of molybdenum (Ti-7.5Mo) was prepared from titanium of 99.9% in purity and molybdenum of 99.95% using a commercial arc-melting vaccum-pressure type casting system (Castmatic, Iwatani Corp., Japan). The melting chamber was first evacuated and purged with argon. An argon pressure of 1.5 kgf/cm² was maintained during melting. Appropriate amounts of metals were melted in a U-shaped copper hearth with a tungsten electrode. The ingot was re-melted three times prior to casting to improve chemical homogeneity.

Prior to casting, the ingot was re-melted again in an open-based copper hearth under an argon pressure of 1.5 kgf/cm². The difference in pressure between the two chambers allowed the molten alloys to instantly drop into the graphite mold when melted.

Figure 13A:
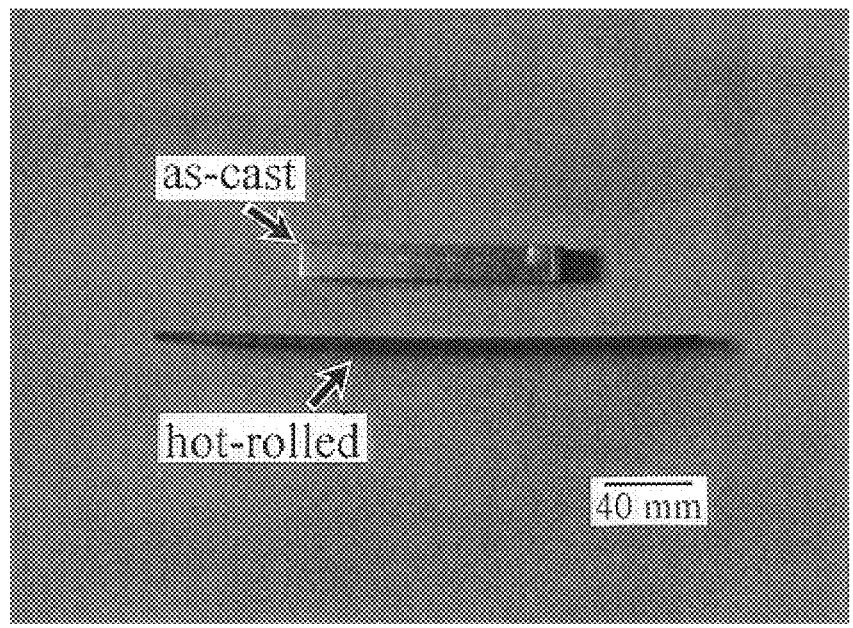
FIG. 13a is a side view of the as-cast specimen and the hot-rolled specimen used in Example 7.
Figure 13B:
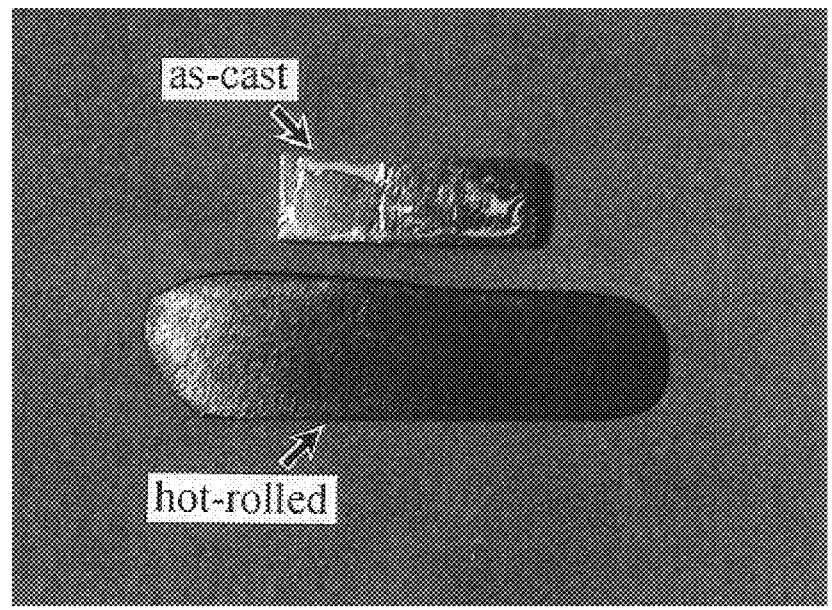
FIG. 13b is a top view of the as-cast specimen and the hot-rolled specimen used in Example 7.
Figure 14A:
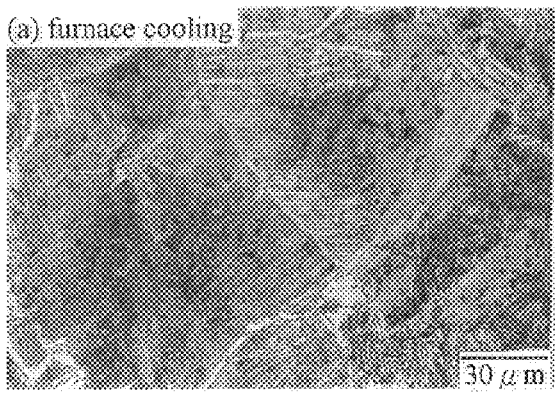
FIG. 14a is a light microscope of the hot-rolled Ti-7.5 Mo which was subjected to furnace cooling.
Figure 14B:
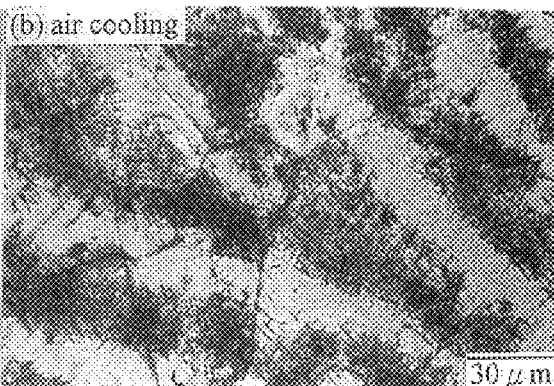
FIG. 14b is a light microscope of the hot-rolled Ti-7.5 Mo which was subjected to air cooling.
Figure 14C:
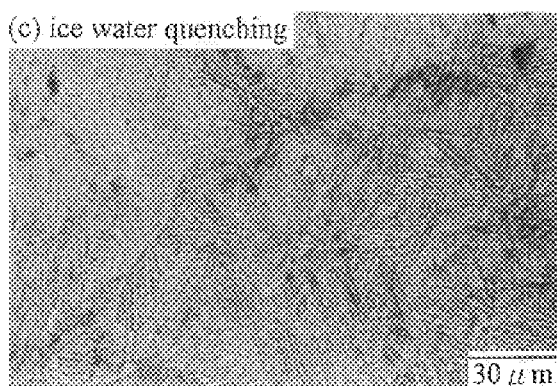
FIG. 14c is a light microscope of the hot-rolled Ti-7.5 Mo which was subjected to ice water quenching.
Figure 14D:
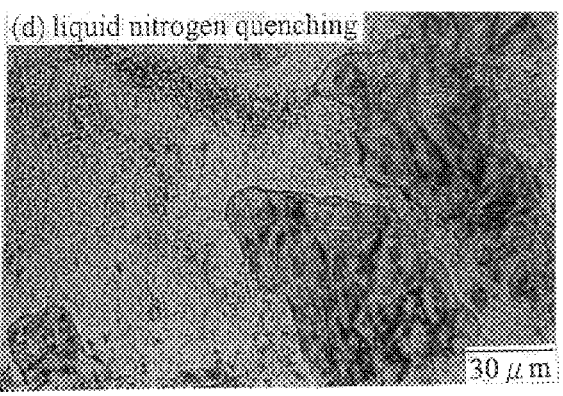
FIG. 14d is a light microscope of the hot-rolled Ti-7.5 Mo which was subjected to liquid nitrogen quenching.
Figure 15:
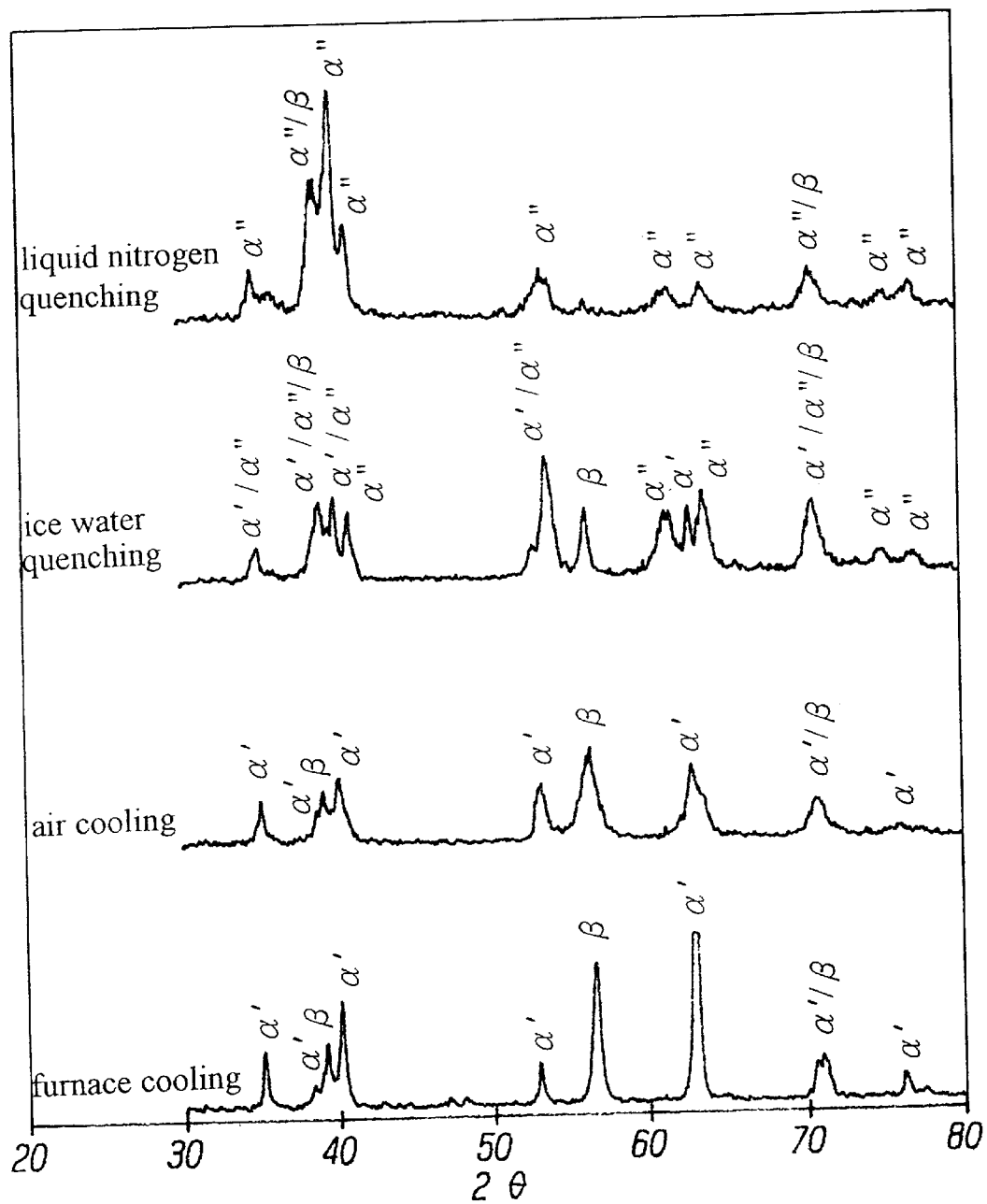
FIG. 15 is a diagram showing XRD patterns of the hot-rolled Ti-7.5 Mo when subject to different cooling process.
Figure 16:
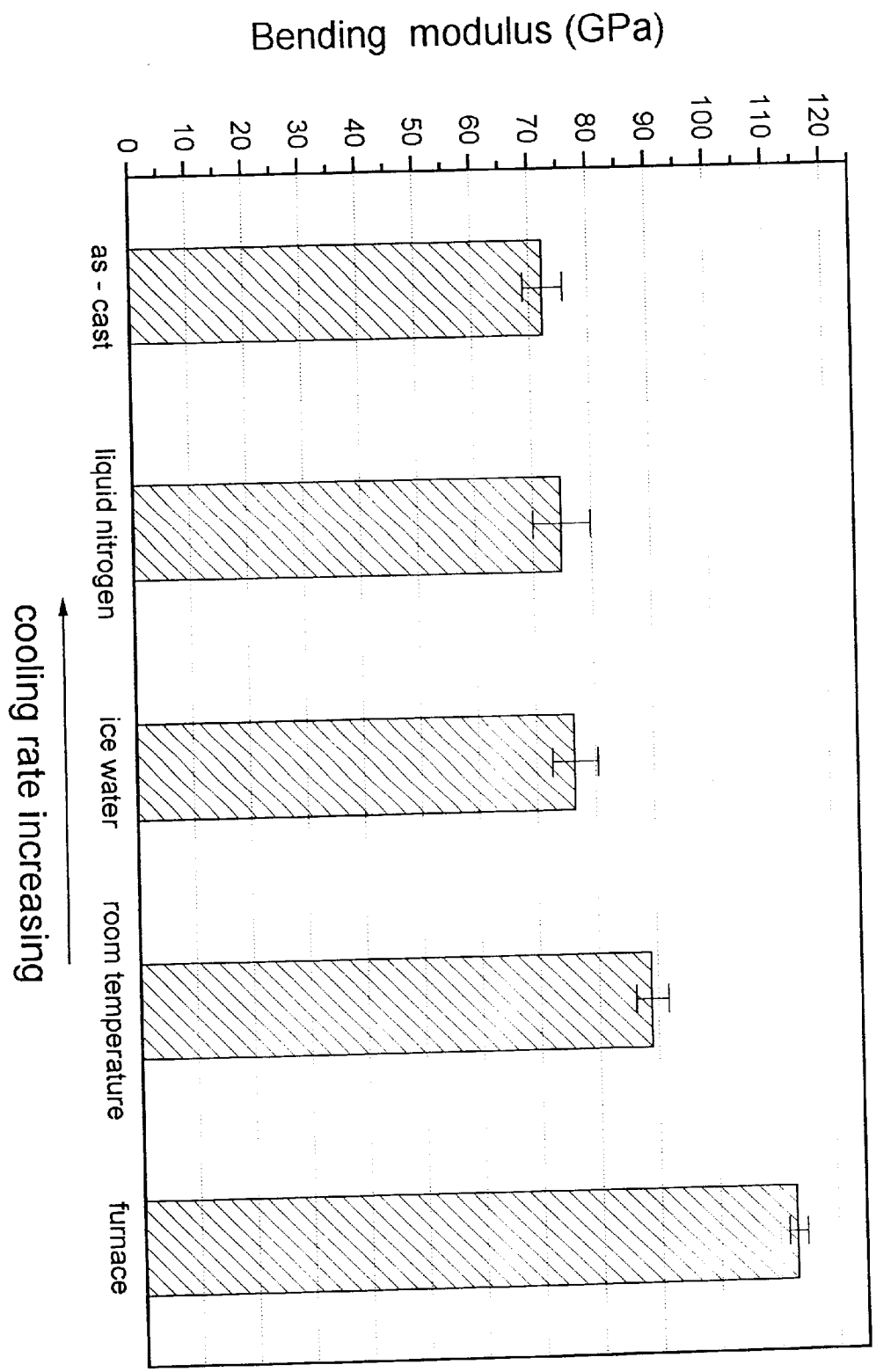
FIG. 16 is a diagram showing the elastic modulus when the cooling rate is increased.

The cast alloy was sectioned using a Buehler Isomet low speed diamond saw to obtain specimens. The alloy specimens were then hot rolled at 900° C. to reduce their thickness by 70% through a single pass. The photographs shown in FIG. 13a and FIG. 13b demonstrate the good high temperature workability of Ti-7.5Mo alloy. The hot-rolled alloy specimens were cooled at four different cooling rates: furnace cooling, room temperature cooling, ice water quenching or liquid nitrogen quenching. The hot-rolled alloy specimens showed no noticeable rolling-induced structural damage. The optical microstructure of the hot-rolled alloys which were respectively subjected to different cooling process was shown in FIGS. 14a–14d. These alloys were tested by the same procedures as set forth in Examples 1–7. It can be seen from FIG. 15 that the above-mentioned hot-rolled Ti-7.5 Mo had a mixed β/α' phase structure when slowly cooled (air-cooled or furnace-cooled). When the hot-rolled alloy was rapidly cooled (ice water or liquid nitrogen quenched), however, α", the desired phase was largely recovered. The recovery of α" phase was also demonstrated by the lower moduli of he rapidly cooled specimens with the same size and shape. As clearly indicated in FIG. 16, the higher the cooling rate, the lower the modulus can be achieved.

Figure 17:
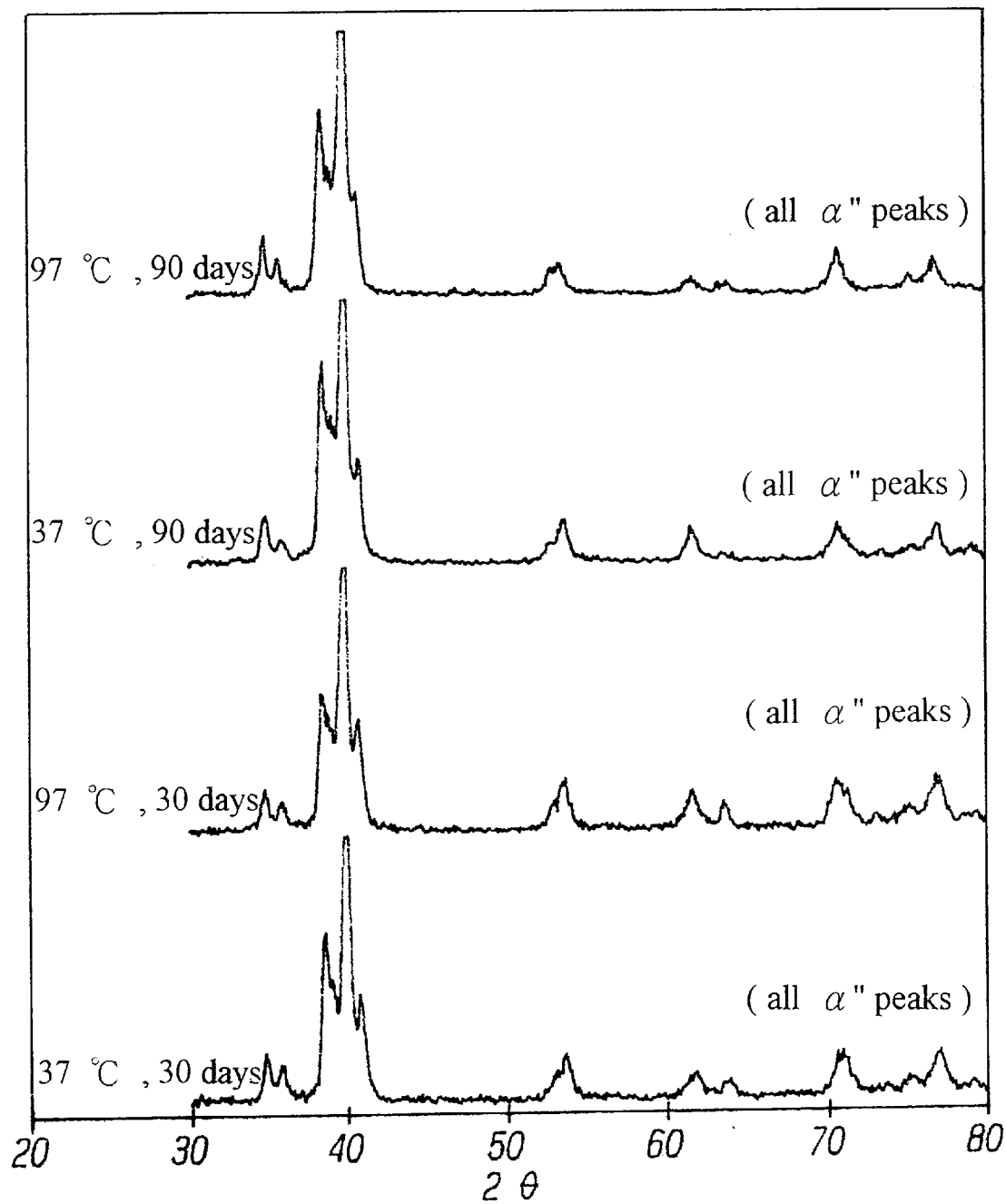
FIG. 17 is a diagram showing the X-ray diffraction patterns when the cast Ti-7.5Mo alloy is immersed in Hank's physiological solution at 37° C. and 97° C. for 30 days or 90 days.

The cast Ti-7.5 Mo alloy with α" phase was also immersed in Hank's physiological solution for up to 3 months at 37° C. (the body temperature) and 97° C. The XRD results in FIG. 17 showed that the α" phase of the alloy was stable even at 97° C. after 90 days.

Figure 18:
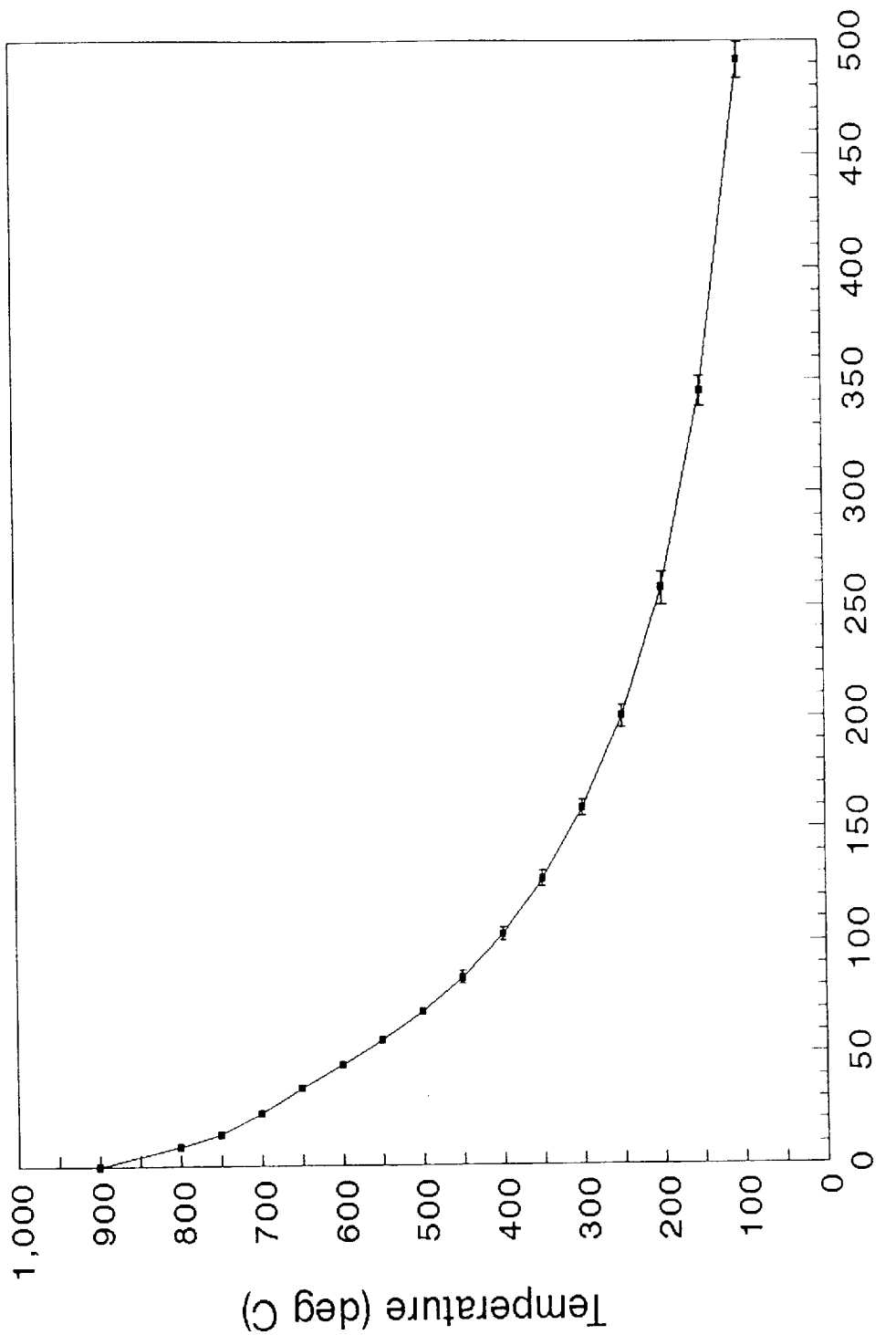
FIG. 18 is a graph showing the cooling rates of air-cooled Ti-7.5Mo specimens.

Although the cooling rates of water or liquid nitrogen-quenched specimens are difficult to determine experimentally, the cooling rates of air-cooled (room temperature) Ti-7.5Mo specimens have been measured. In doing the measurement a thermocouple was inserted into a 5 mm thick Ti-7.5Mo specimen. The thermocouple was positioned to keep a distance within 1 mm to the surface of the specimen. As soon as the thermocouple-inserted specimen was removed from the furnace at 900° C., the temperature of the specimen and cooling time were continually recorded. The data shown in FIG. 18 and Table 4 are averages of eight measurements. As indicated in Table 4, the average cooling rates of the Ti-7.5Mo specimen were 11.5° C./s in the temperature range of 900–800° C.; 6.8° C./s in the range 800–700° C.; 4.6° C./s from 700 to 600° C.; 4.2° C./s from 600 to 500° C.; and so forth. Since the cooling rate of the air cooling process was still not high enough to obtain the α" phase, it is reasonable to conclude that the cooling rate for obtaining α" phase should be higher than roughly 10° C./s.

TABLE 4

| Temperature range | 900–800 | 800–700 | 700–600 | 600–500 | 500–400 | 400–300 | 300–200 | 200–100 |
|---|---|---|---|---|---|---|---|---|
| Average cooling rate (° C./s) | 11.5 | 6.8 | 4.6 | 4.2 | 2.9 | 1.8 | 1.0 | 0.4 |

EXAMPLE 11

Biocompatibility of Ti-7.5Mo alloy was evaluated by directly implanting cast Ti-7.5Mo rods into prepared bone cavities of Taiwan native goats. Cylindrical-shaped Ti-7.5Mo rods with 5.8 mm in diameter and 25 mm in length were prepared using the same casting procedure set forth in Example 10. After casting, the surface of the alloy rods were sand-blasted using 50 μm $Al_2O_3$ particles. The sand-blasted Ti-7.5Mo rods were cleaned in 95% alcohol in an ultrasonic cleaner for 30 minutes and sterilized at 90° C. for 8 hours prior to operation. The Taiwan native goats were anesthetized with intravenous ketamin under a standard aseptic procedure. Bone cavities of 6.7 mm in diameter were prepared by drilling through the bicortical bone on coronary plane. The sterilized Ti-7.5Mo rods were then implanted into the diaphysis portion of either femur or tibia bone by thumb compression. When femur bone was selected as implant site, bone cavities were prepared via lateral approach. When tibia bone was selected, bone cavities were prepared via anterior approach.

The goats were sacrificed after 15 weeks by overdose ketamin. The femur and tibia bone structure along with the embedded implants were dissected out for evaluation. The bone/implant composite specimens were fixed in neutralized formalin and sectioned using an EXACT BS-300U diamond saw. The bone-implant interface regime was examined using a TOPCON-SM-300, low vacuum scanning electron microscope (LVSEM). Using this low vacuum SEM the specimens could be examined under a "wet" condition and the conventional coating of a conducting film on specimen surface was not needed.

Figure 19:
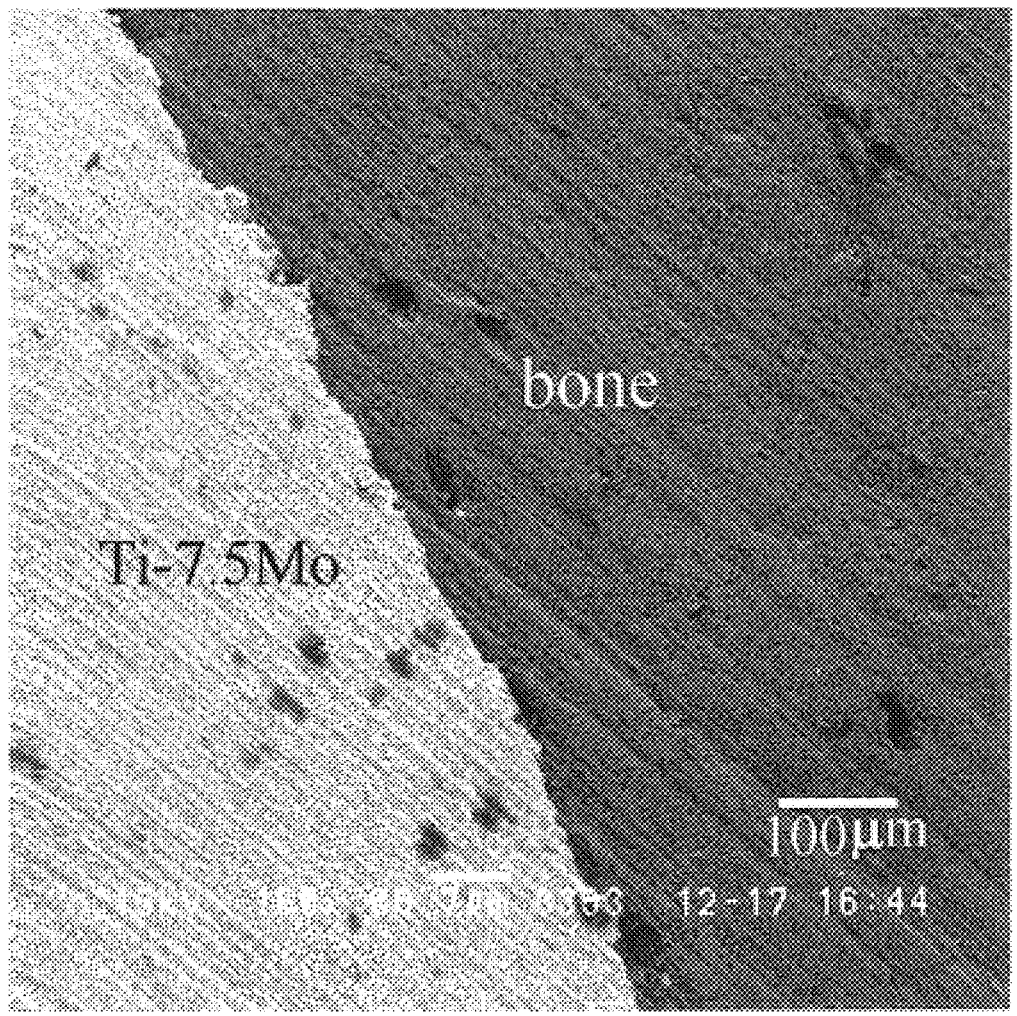
FIG. 19 is a LVSEM micrograph showing the new in-growing bone structure filled between Ti-7.5Mo implant and cortical bone according to Example 11.

The LVSEM examination showed that the initial gaps between implant and bone structure were almost completely filled by new in-growing bone structure. An example is given in FIG. 19. Clearly shown in this LVSEM micrograph, the initial 520 μm wide gap between the Ti-7.5Mo implant and the cortical bone was entirely filled out by new in-growing laminar cortical bone structure. Results of this implant study indicate that Ti-7.5Mo alloy is highly biocompatible with excellent binding capability with bone structure.

What is claimed is:

1. A medical implant consisting essentially of a biocompatible titanium alloy containing α" phase as a major phase, said alloy consisting essentially of from about 6 to about 9 wt % of molybdenum, from 0 to 1 wt % of an alloying element and the balance titanium, wherein said alloying element is selected from the group consisting of niobium, zirconium and the mixture thereof.

2. The medical implant of claim 1, wherein the alloy contains about 7.5 wt % of molybdenum.

3. The medical implant as claimed in claim 1, wherein the alloy contains 1 wt % of said alloying element.

4. The medical implant as claimed in claim 3, wherein said alloying element is niobium.

5. The medical implant as claimed in claim 3, wherein said alloying element Is zirconium.

6. The medical implant as claimed in claim 1 which is an orthopedic implant.

7. The medical implant as claimed in claim 1 which is a dental implant, dental crown, dental bridge, or a denture framework.

8. A medical implant consisting essentially of a biocompatible titanium alloy containing α" phase as a major phase, said alloy consisting essentially of from about 6 to about 9 wt % of molybdenum, and the balance titanium.

9. The medical implant as claimed in claim 8, wherein the alloy contains about 7.5 wt % of molybdenum.

10. The medical implant as claimed in claim 8 which is an orthopedic implant.

11. The medical implant as claimed in claim 8 which is a dental implant, dental crown, dental bridge, or a denture framework.

* * * * *

UNITED STATES PATENT AND TRADEMARK OFFICE
CERTIFICATE OF CORRECTION

PATENT NO.    : 6,409,852 B1
DATED         : June 25, 2002
INVENTOR(S)   : Lin et al.

It is certified that error appears in the above-identified patent and that said Letters Patent is hereby corrected as shown below:

<u>Title page,</u>
Item [73], please correct the first Assignee's name to:
-- Jiin-Huey Chern LIN, Kaoshiung; --

Signed and Sealed this

Thirty-first Day of December, 2002

JAMES E. ROGAN
*Director of the United States Patent and Trademark Office*